(12) United States Patent
Zentner et al.

(10) Patent No.: US 6,537,584 B1
(45) Date of Patent: Mar. 25, 2003

(54) POLYMER BLENDS THAT SWELL IN AN ACIDIC ENVIRONMENT AND DESWELL IN A BASIC ENVIRONMENT

(75) Inventors: Gaylen M. Zentner, Salt Lake City, UT (US); Jong-Seok Bark, Salt Lake City, UT (US); Feng Liu, Salt Lake City, UT (US)

(73) Assignee: MacroMed, Inc., Sandy, UT (US)

( * ) Notice: Subject to any disclaimer, the term of this patent is extended or adjusted under 35 U.S.C. 154(b) by 5 days.

(21) Appl. No.: 09/710,403

(22) Filed: Nov. 9, 2000

Related U.S. Application Data

(63) Continuation-in-part of application No. 09/438,884, filed on Nov. 12, 1999, now abandoned.

(51) Int. Cl.$^7$ .............................................. A61K 9/50
(52) U.S. Cl. ..................... 424/499; 424/484; 424/486; 424/488; 424/489; 424/502; 514/772; 514/772.1; 514/772.2; 514/772.3; 514/772.6
(58) Field of Search ............................. 514/772, 772.1, 514/772.2, 772.3, 772.6, 844; 424/484, 486, 488, 489, 499, 501

(56) References Cited

U.S. PATENT DOCUMENTS

| | | | |
|---|---|---|---|
| 4,034,756 A | | 7/1977 | Higuchi et al. |
| 4,320,759 A | | 3/1982 | Theeuwes |
| 4,503,030 A | | 3/1985 | Edgren et al. |
| 4,627,850 A | | 12/1986 | Deters et al. |
| 4,717,566 A | | 1/1988 | Eckenhoff et al. |
| 4,743,247 A | | 5/1988 | Wong |
| 4,783,337 A | | 11/1988 | Wong et al. |
| 4,814,180 A | | 3/1989 | Eckenhoff et al. |
| 4,837,111 A | | 6/1989 | Deters et al. |
| 4,865,598 A | | 9/1989 | Eckenhoff |
| 4,871,544 A | | 10/1989 | Eckenhoff |
| 4,883,667 A | | 11/1989 | Eckenhoff |
| 4,948,592 A | | 8/1990 | Ayer et al. |
| 4,966,767 A | | 10/1990 | Eckenhoff |
| 5,226,902 A | | 7/1993 | Bae et al. |
| 5,420,197 A | * | 5/1995 | Lorenz et al. .............. 525/54.3 |
| 5,620,706 A | | 4/1997 | Dumitriu et al. |
| 5,770,712 A | | 6/1998 | Roy et al. ..................... 536/20 |
| 5,773,608 A | * | 6/1998 | Yen et al. ..................... 536/124 |
| 5,864,025 A | | 1/1999 | Glasser et al. ................ 536/20 |
| 5,904,927 A | | 5/1999 | Amiji |

OTHER PUBLICATIONS

Sei–ichi Aiba, Studies on Chitosan: 3. Evidence for the Presence of Random and Block Copolymer Structures in Partially N–acetylated Chitosans, Int. J. Biol. Macromol., 1991, vol. 13, Feb., Biomimetic Chemistry Division, Industrial Products Research Institute, I–I–4 Higashi, Tsukuba, Ibaraki 305, Japan.
Kjell M. Varum, Marit W. Anthonson, Hans Grasdalen and Olay Smidsrod, Determination of the Degree of N–acetylation and the Distribution of N–acetyl groups in Partially N–deacetylated Chitins (Chitosans) by High–field n.m.r. Spectroscopy, Norwegian Biopolymer aboratory (NOBI-POL), Division of Biotechnology, The Norwegian Institute of Technology (NT11), The University of Trondheim, 7034 Trondheim (Norway).
Attila E. Pavlath, Dominic W. S. Wong, and George H. Robertson; Western Regional Research Center Agricultural Research Service, U.S. Department of Agriculture; Chitosan, Preparation, Structure and Properties, 1996 by CRC Press, Inc.
Applications and Properties of Chitosan; Q. Li, E. T. Dunn, E. W. Grandmaison and M.F.A. Goosen, Department of Chemical Engineering, Queen's University, Kingston, Ontario, Canada; Applications and Properties of Chitosan.

* cited by examiner

*Primary Examiner*—Thurman K. Page
*Assistant Examiner*—Liliana Di Nola-Baron
(74) *Attorney, Agent, or Firm*—Thorpe North & Western, LLP

(57) ABSTRACT

A polymer blend is prepared by dissolving chitosan and a second polymer in an acidic aqueous solution to form an aqueous polymer blend, dehydrating said aqueous polymer blend, and recovering said polymer blend. The second polymer may be selected from the group consisting of polyether glycols including polyethylene glycols; cellulose esters including cellulose acetate; poloxamers; polysaccharides including dextran and guar; polyvinylpyrrolidones; polyvinyl alcohols; and mixtures or copolymers thereof. These polymer blends swell in an acidic environment and deswell in a more neutral or basic environment. This technology is valuable for the dispensing of biologically active material or drugs into a surrounding environment, especially the environment as is found in the gastrointestinal tract. Since the various polymer blends of the present invention are not covalently or ionically crosslinked, but are physically combined, each polymer in the physical blend maintains its original chemical structure, and therefore, is safe for oral administration.

66 Claims, No Drawings

POLYMER BLENDS THAT SWELL IN AN ACIDIC ENVIRONMENT AND DESWELL IN A BASIC ENVIRONMENT

This is a continuation-in-part of U.S. application Ser. No. 09/438,884 now abandoned, filed on Nov. 12, 1999.

FIELD OF THE INVENTION

The present invention relates to various polymer blends that, when exposed to aqueous conditions, become hydrogels. These hydrogels are used for carrying and delivering bioactive agents or drugs in a biological environment. More specifically, the invention relates to polymer blends that, when exposed to aqueous conditions, form hydrogels that swell when exposed to an acidic environment (such as that found in the stomach) and deswell when exposed to a more neutral to alkaline environment (such as that found in the small and large intestines). When the hydrogel swells and deswells, the release of biologically active material contained in the hydrogel is modulated.

BACKGROUND OF THE INVENTION

There have been many approaches to meet the problems of regulating the delivery of bioactive agents or drugs to biological systems in the proper place, at the proper time and at the proper dose to achieve a desired effect. These systems depend on the utilization of physical or chemical stimuli in the surrounding environment. Further, these environmental stimuli are usually of an external nature to the drug delivery system. Mechanisms that respond to such stimuli or signals include protein binding, hydrogel expanding or swelling, polymer erosion, membrane reorganization, solubility change, energy conversion, supply of activation energy for permeation, physical property changes of the materials that comprise the system, or phase transition phenomena, and the like. Examples are presented by Heller, Chemically self-regulated drug delivery systems, J. Control. Rel., 8, 111–125 (1988).

Particularly, gels have been used to deliver biologically active material to biological environments. For example, U.S. Pat. No. 4,034,756 is drawn to a device having two compartments, one filled with an osmotic agent or gel that swells in the presence of water and the other filled with a bioactive drug or other material. The expanding of the osmotic agent compartment or swelling of the gel forces the material contained in the second compartment through an orifice. A flexible partition between the two compartments acts to force the material in the second compartment through the orifices.

Other exemplary art includes U.S. Pat. Nos. 4,627,850; 4,717,566; 4,783,337; 4,743,247; 4,814,180; 4,837,111; 4,865,598; 4,871,544; 4,883,667; and 4,966,767, none of which have a flexible partition between the two compartments. The systems disclosed in these patents rely on the expanding of the osmotic agent compartment or gel swelling to force the drug out through orifices or a permeable membrane.

U.S. Pat. No. 4,320,759 includes additional partitioning membranes. U.S. Pat. Nos. 4,871,544 and 4,966,767 include osmotic agents to enhance the expanding or swelling of the gels. Osmotic agents are also mixed with beneficial agent formulations in the second compartment in the systems taught in U.S. Pat. Nos. 4,783,337 and 4,837,111. Some patents reveal the inclusion of a density member to keep the devices in an aqueous environment. The density member is dispersed in the expandable hydrogel compartment (U.S. Pat. Nos. 4,783,337 and 4,837,111) or in separate compartments (U.S. Pat. Nos. 4,717,566 and 4,865,598) that are placed in different locations in relation to other compartments.

U.S. Pat. No. 4,503,030 shows pH responsive release, that is, controlled release at low pH, but dumping of all remaining agents at high pH by disintegration of the devices. This action cannot be repeated with subsequent pH changes. U.S. Pat. No. 4,948,592 demonstrates a two mode release pattern, that is a one time burst releasing the beneficial agents at the beginning followed by a controlled release. This is based on the dissolution of a coating layer covering the osmotic devices, containing beneficial agents for quick release, followed by the timed sustained release of agents from the inner compartment of the device by osmotic squeezing. U.S. Pat. Nos. 4,814,180 and 4,871,544 contain temperature responsive materials in the devices disclosed. This material delivers the agent at body temperature with no release at storage temperature. At room or storage temperature, the material remains in the solid state, preventing squeezing of agents from the devices in the presence or absence of environmental water. However, at body temperature the material becomes a liquid allowing the formulation containing the beneficial agents to flow that can then be pushed out via a passageway(s) by osmotic force. A contracting or deswelling hydrogel for drug delivery purposes has been reported by Hoffman et al. J. Control. Rel., 4, 213–222 (1986). A temperature sensitive hydrogel was synthesized that deswelled at elevated temperatures and swelled at low temperatures. Vitamin B12 was entrained at a low temperature and released at a higher temperature by a deswelling or squeezing action. However, the overall release rate was quick and vitamin B12 was released in two steps; a fast squeezing and subsequent slow release due to a rigid surface formation on the hydrogel. It is expected that the release of the entrained drug from the unprotected hydrogel at low temperatures will be unacceptably high. Therefore, this system may not be suitable for repeated pulsatile drug release by temperature modulation.

The opposite release pattern from a monolithic device was reported by Bae et al., Makromol. Chem Rapid Commun., 8, 481–485 (1987) in which a pulsatile release was demonstrated using N-isopropylacrylamide based thermo-sensitive hydrogels (see also Hoffman et al, J. Control. Rel., 4, 213–222 (1986)). These polymers showed immediate rigid surface formation with contracting or deswelling process when the temperature was raised. This phenomenon blocks solute release from the gel matrices at an elevated temperature while allowing solute release at a low temperature. J. Kost (Ed.), Pulsed and Self Regulated Drug Delivery, CRC Press Inc., Boca Raton, Fla., (1990), Chapter 2, Temperature Responsive Control Drug Delivery, (authored by the present inventors) discloses the formation of a gel that expands or swells and contracts or deswells according to the temperature changes. This article indicates that the gel was used to entrain drug solutions but does not disclose or suggest that the gel can be contained within or used in a structured drug delivery device.

However, one patent, namely U.S. Pat. No. 5,226,902 which is incorporated herein by reference, does teach a beneficial agent in a hydrogel confined to a structured dispensing device that, when exposed to stimuli, forces the agent by contracting or deswelling into the space within the device previously occupied by the swollen hydrogel allowing the beneficial agent to be released from the device into the surrounding environment.

All of the pH sensitive synthetic hydrogels presently known in the art are covalently crosslinked. Though the use of covalently crosslinked pH sensitive hydrogels that deswell at physiological pH and swell at stomach pH were disclosed previously in U.S. Pat. No. 5,226,902, no specific polymer blend has been disclosed that exhibits these properties, i.e., rapidly swells in acidic conditions, slowly/extensively deswells in more basic conditions, contains no covalent crosslinking, is insoluble in acid and is safe for oral delivery among other properties.

In U.S. Pat. No. 5,904,927, a drug-delivery device is disclosed which is comprised of a cationic polymer such as chitosan and a second high molecular weight neutral polymer such as polyethylene oxide which is covalently crosslinked, freeze-dried and loaded with a drug composition. This drug delivery polymer composition is prepared using a low concentration of acetic acid (0.1 N) and is covalently crosslinked changing the properties of each individual polymer in the composition.

Additionally, in U.S. Pat. No. 5,620,706, insoluble hydrogels are disclosed which are comprised generally of xanthan and chitosan. Xanthan is a polysaccharide anion which is soluble in cold or hot water, but is not soluble in organic solvents. Xanthan (anionic) and chitosan (cationic) form an tonically bonded complex. The patent states that hydrogels containing chitosan are stable at acidic pH levels and that the hydrogels may be in the form of microspheres, spheres, films, and sponges. Gels having different properties may be produced by using different xanthan to chitosan ratios and/or chitosan having different degrees of acetylation. However, this invention may only be practiced by pre-loading the gel with the drug and then drying prior to delivery.

In light of the prior art, it would be useful to provide a polymer blend comprised of chitosan and a second polymer that may be used for drug delivery which blend does not alter the properties of the individual polymers by covalent cross linking, nor relies on ionic interactions to form the gel.

OBJECTS AND SUMMARY OF THE INVENTION

It is an object of the present invention to provide various polymer blends that are not covalently or ionically crosslinked that, when exposed to aqueous conditions, swell in acidic conditions and deswell in more neutral to basic conditions.

It is another object of the present invention to provide various polymer blends that may be used for controlled bioactive agent or drug delivery by loading the polymer blend with a desired bioactive agent or drug, or mixing the polymer blend with bioactive agents or drugs, and modulating that bioactive agent or drug release profile to appropriate tissue.

It is still another object of the present invention to provide polymer blends that, once hydrated, become rigid hydrogels that are substantially insoluble in acidic conditions, or at least remain rigid in acidic conditions for a sufficient period of time to carry out its purpose of modulating drug delivery.

A still further object of the invention is to provide various non-toxic polymer blends that are suitable for oral delivery by blending chitosan and a second polymer together in the presence of an acid, wherein each of the polymers alone do not exhibit gelation characteristics, and as a blend, forms gels that are not covalently or ionically bonded or crosslinked.

Another object of the present invention is to provide drug containing polymer blends for oral delivery that are sensitive to external conditions, e.g., when the polymer blend reaches the stomach (pH 1 or 2), the polymer blend hydrates and swells, and when the hydrogel reaches the intestinal track (pH 7 or 8), the hydrogel deswells to modulate release of the bioactive agent or drug into the intestinal track.

Another object of the present invention is to provide drug containing polymer blends for oral delivery of soluble bioactive agents or drugs that are sensitive to external conditions, but may also be controlled internally, e.g., by employing additives and/or excipients used to either increase or retard swelling.

Still another object of the present invention is to utilize such polymer blends or hydrogels within a drug delivery device designed with walls having a means of allowing external or internal conditions to be sensed by the hydrogel within and likewise, having the ability to allow the bioactive agent or drug that has been either loaded into the hydrogel or mixed with the hydrogel to be released through the walls.

These objects and others may be obtained by blending chitosan with a second polymer selected from the group consisting of polyether glycols (e.g., polyethylene glycols), cellulose esters (e.g., cellulose acetate), poloxamers, polysaccharides (e.g., dextran and guar), polyvinylpyrrolidones, polyvinyl alcohols, and mixtures or copolymers thereof to form polymer blends that, once hydrated, are useful for bioactive agent or drug delivery.

It is necessary that these polymer blends, once hydrated to form a hydrogen, exhibit properties that make them either substantially insoluble in acid or, if soluble, that the hydrated polymer blends or hydrogels remain rigid in acidic conditions for a sufficient period of time to carry out their purpose of modulating bioactive agent or drug delivery. The polymer blends of the present invention are prepared by (a) admixing chitosan with one or more of the other polymers or copolymers in the presence of an acid, (b) substantially drying the mixture by exposure to air at room temperature or elevated temperature, exposure to a vacuum, spray drying, or any combination thereof, and (c) recovering the polymer blend. The polymer blend may be mixed with a bioactive agent or drug as a powder, or the polymer blend may be hydrated in a solution containing the bioactive agent or drug whereby the drug is loaded into the hydrogel matrix. Alternatively, the drug and all polymers may be dissolved and then isolated together as the mixture is dried. Thus, the loading process may occur simultaneous with or after the polymer blend is formed.

One embodiment provides that the polymer blend described be used within a device having a wall defining an interior compartment for dispensing of biologically active material or drug into a surrounding environment such as that disclosed in U.S. Pat. No. 5,226,902, the entire teachings of which are incorporated herein by reference. However, this embodiment is not intended to be limiting as the invention may be used without such a device or in conjunction with any other appropriate delivery device.

DETAILED DESCRIPTION OF THE INVENTION

Before the present invention and method of making and delivering the same is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

Further, it should be understood that chitosan is a natural product derived from chitin, a polysaccharide often found in the exoskeleton of shellfish such as shrimp or crabs. Chitin is a naturally occurring substance that may be regarded as a derivative of cellulose in which the C-2 hydroxyl groups have been replaced by acetamido residues. Chitin is predominantly unbranced chains of β-(1–4)-2-acetamido-2-deoxy-D-glucose residues. Chitosan is formed by deacetylation of chitin. The degree of deacetylation usually ranges from 70% to 95%, depending on the method of deacetylation used. However, in most publications, chitosan is said to exist when chitin has been deacetylated by more than 70% (Q. Li, et. al., J. Bioactive and Compatible Polymers, Volume 7, Page 372, October 1992). This amount of deacetylation yields a water-soluble polymer when the pH is less than 6.5. However, heterogeneous processing can result in deacetylation in blocks rather than in a random manner. Alternatively, by substantial deacetylation and reacetylation, a more randomly acetylated chitosan can be formed. Under these conditions, as low as 50% deacetylation (random) can result in a soluble chitosan at essentially neutral pH. With this explanation in mind, chitosan is generally a random copolymer whose structure may be represented by Formula 1 below:

Formula 1

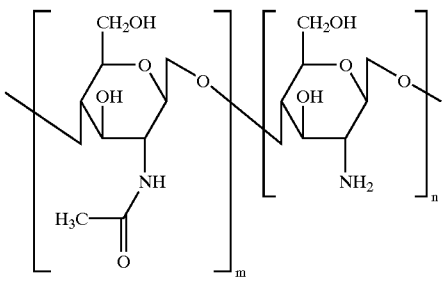

where n groups comprise ≧50% and m groups comprise ≦50% of the copolymer repeat units. Though the deacetylation range can be from about 50% to 95%, preferably, the n groups are from 70% to 95%.

"Brookfield viscosity" is defined as the internal friction of a fluid, caused by molecular attraction, which makes it resist a tendency to flow. With respect to the present invention, the Brookfield viscosity for chitosan can range from approximately 100 cps to 10,000 cps. Chitosan, being a long linear polymer, forms a viscous solution. Molecular weight and viscosity are related, and thus, viscosity is an indirect measurement of molecular weight.

To avoid confusion, the standard operating procedures for determining the Brookfield viscosity for each chitosan sample is provided. An LVT viscometer was used for all viscosity data taken, and the steps were as follows: 1) prepare a chitosan solution comprising 1% chitosan and 1% acetic acid and fill a plastic bottle ¾ full of the chitosan solution; 2) insert a thermometer and read the temperature, and if the temperature is not 25° C., the solution is cooled in a cold water bath or warmed in a warm water bath as needed to reach 25° C. (+/−0.5° C.); 3) ensure that the solution is relatively free of bubbles; 4) insert a proper spindle into the solution bottle at a tilted angle to prevent the trapping of air bubbles underneath the spindle (spindle 1 is used for 1–100 viscosity range; spindle 2 is used for 100–1000 viscosity range; spindle 3 is used for 1000–4000 viscosity range; and spindle 4 is used for >4000 viscosity range); 5) lower the viscometer unit until the spindle can remain in the solution and then screw the spindle into the viscometer; 6) raise or lower the viscometer head with the armature knob so that spindle notch is even with solution level; 7) level the viscometer head by raising or lowering appropriate movable feet; 8) turn on the viscometer and then set it to 30 rpm; 9) if the solution is of higher or lower viscosity, change the spindle so that the dial reads between 10 and 100 at 30 rpm; 10) let the spindle rotate for 5 minutes; 11) depress the lever in the back of the viscometer unit to lock the dial arm when the dial appears in the viewable window; 12) turn off the viscometer; 13) read the dial and multiplier from appropriate spindle number/speed chart; 14) multiply the dial reading by the multiplier and record the calculated viscosity. The Brookfield viscosity (cps) is measured as the reading on the viscometer dial is multiplied by the appropriate multiplier. It is important that the viscosity is measured within 20 minutes after finishing the solution preparation procedure of step 1.

Polyethylene glycol (PEG) is a polymer chain having the formula structure $H[OCH_2CH_2]_mOH$ where m is from about 20 to approximately 100,000. These values of m correspond to weight average molecular weights (Mw) of aproximately 1,000 to 4,000,000. PEG is essentially the same structure as polyethylene oxide (PEO), the only difference being the structure found at the end groups. However, both are considered to be within the group of polyether glycols for purposes of the present invention.

Cellulose esters (e.g., cellulose acetate), poloxamers, polysaccharides (e.g., dextran and guar), polyvinylpyrrolidones, and polyvinyl alcohols are also polymers that form acceptable polymer blends when mixed with chitosan. Mixtures or copolymers of polyether glycols, cellulose esters, poloxamers, polysaccharides, polyvinylpyrrolidones, and polyvinyl alcohols are also included and form acceptable polymer blends when mixed with chitosan.

"Biocompatible" shall mean any substance or blend that is not toxic to the body at levels and concentrations that are functional for the purposes of this invention.

"Bioactive agent" or "drug" shall mean any drug, organic compound, substance, nutrient or biologically beneficial agent including proteins, peptides(including polypeptides and oligopeptides), hormones, vaccines, oligonucleotides, genes, nucleic acids, steroids, antibiotics, antibodies, viruses, live cells and other chemotherapeutic or non-therapeutic agents without limitation.

"Polymer blend" is meant to include mixtures of chitosan and a second polymer that are not covalently or ionically crosslinked. The second polymer is preferably selected from the group consisting of polyether glycols, cellulose esters, poloxamers, polysaccharides, polyvinylpyrrolidones, polyvinyl alcohols, and mixtures or copolymers thereof.

"Drug containing polymer blend" is meant to cover both drug loaded polymer blends as well as polymer blends that are simply admixed with a drug. In either case, the polymer blend at hydration forms a hydrogel that modulates the release of the drug.

"Acidic environment," "acidic conditions," or "acidic pH level" is intended to cover all pH levels less than 7. However, for purposes of the present invention, pH levels from about 0.1 to about 6 are the most preferred pH levels that may be used to swell the polymer blends of the present invention.

"More neutral to basic environment," "alkaline environment," "basic conditions,." or "basic pH level," is meant to include pH levels from about 7 to about 14.

"Warm-blooded animal" or "warm-blooded mammal" are meant to include humans as well as other warm-blooded species of the animal kingdom.

A variety of polymers may be blended with chitosan to form non-covalently or non-ionically bonded polymer blends. These polymer blends, when prepared properly, are unique in several ways. First, because the polymer blends (chitosan blended with polyether glycols, cellulose esters, poloxamers, polysaccharides, polyvinylpyrrolidones, polyvinyl alcohols, and mixtures or copolymers thereof) are not covalently or ionically cross linked, but are physically combined, each polymer in the physical blend maintains its original chemical structure, and therefore, is safe for oral or other routes of administration. Second, stable polymer blends are either insoluble or at least dissolve slowly in acidic and/or basic conditions. Third, these hydrogels exhibit unique swelling and deswelling properties that have not been found previously in synthetic hydrogels without covalent cross linking. Additionally, most known hydrogels exhibit swelling in neutral to basic conditions and deswelling in acidic conditions which is opposite in behavior to the hydrogels of the present invention. Because the polymer blends are not covalently or ionically crosslinked, but are physically blended, and because the hydrated polymer blends or hydrogels swell in more acidic environments (preferably at pH levels from about 0.1 to 6) and deswell in more neutral to alkaline environments (preferably at pH levels from about 7 to 14), the polymer blends of the present invention are unique and useful for bioactive agent or drug delivery through oral ingestion and other routes of administration.

These polymer blends can be manufactured under various conditions, ratios and dehydration times. Further, the polymer blends of the present invention can also be manufactured using various concentrations of the acid component as well as various Brookfield viscosities or weight average molecular weights (Mw) and ratios of the individual polymers.

To create these polymer blends, chitosan is dissolved and blended with a second polymer(s) in an appropriate acidic solution. The weight ratio of chitosan to the second polymer (s) may be about 1:4 to 10:1 (preferably 1:1 to 5:1) to form an acceptable polymer blend. Various concentrations of the acid solution may also be used. For example, if acetic acid is used, a concentration from about 0.5 M to 11 M is appropriate, depending on which second polymer(s) is blended or mixed with the chitosan. A preferable range of acetic acid concentration is generally from 1 M to 2 M for blends and mixtures of chitosan and polyether glycols, poloxamers, polysaccharides, polyvinylpyrrolidones, polyvinyl alcohols, and mixtures and copolymers thereof. A preferable range of acetic acid concentration is from 8 M to 11 M for blends and mixtures of chitosan and cellulose esters. Additionally, citric acid, hydrochloric acid and/or other organic or inorganic acids may also be used at concentrations ascertainable by those skilled in the art.

Polymers of various weight average molecular weights (Mw) (or Brookfield viscosity with respect to chitosan) can also be used. For example, chitosan having a Brookfield viscosity from 100 cps to 10,000 cps, preferably from 440 cps to 1370 cps can be used. Regarding the weight average molecular weight of the second polymer(s), representative examples include: PEG from about 1,000 to 4,000,000 Mw, preferably from 1,000 to 6,000 Mw; cellulose acetate from about 10,000 to 50,000 Mw; poloxamer from about 1,000 to 12,000 Mw; dextran from about 10,000 to 4,000,000 Mw; polyvinylpyrrolidones from about 10,000 to 1,000,000 Mw; and polyvinyl alcohols from about 5,000 to 200,000 Mw.

Once the polymer blend is dissolved under the selected acidic conditions, at the selected ratio, and at the selected weight average molecular weights (Mw) or viscosities (cps), the mixture or blend is dried or dehydrated. Drying or dehydration can occur at room or elevated temperature, i.e., up to about 70° C., subject to open air conditions, exposure to a vacuum, spray drying, etc., in any combination thereof followed by recovery of the polymer blend. The polymer blend is then cut, pulverized, or milled into appropriate sizes suitable for combination with one or more bioactive agents or drugs.

The polymer blend may be blended with the bioactive agent or drug as a powder, or the polymer blend may be hydrated in a solution containing bioactive agent or drug. Alternatively, the drug and all polymers may be dissolved and then isolated together as the mixture is dried. Preferably, the combined drug and polymer blend is then encased in a drug delivery device, such as that described in U.S. Pat. No. 5,226,902, for oral or other route of administration, though a drug delivery device is not required. It is important to note that the bioactive agents or drugs entrained in or mixed with the polymer blend should be sufficiently soluble in an aqueous solution to diffuse or convectively move in the aqueous media of the surrounding environment at an amount that is therapeutically relevant.

The invention is not limited to the use of any type or class of bioactive agent, drug or other pharmaceutical agent as long as it is functional for use in the polymer blends of the present invention. Bioactive agents or drugs suitable for use in the hydrogels disclosed herein are listed in standard publications including *Remington's Pharmaceutical Sciences* and *The Merck Index* or Physicians *Desk Reference*. However, preferred classes of bioactive agents or drugs may be organic or inorganic compounds or substances, nutrients or biologically beneficial agents including proteins, peptides (including polypeptides and oligopeptides), hormones, vaccines, viruses, oligonucleotides, genes, nucleic acids, steroids, antibiotics, antibodies, live cells, and other chemotherapeutic or non-therapeutic agents. The functionality of any given bioactive agent or drug may be readily determined by those skilled in the art.

The swelling and deswelling properties of these hydrated polymer blends or hydrogels may be a function of the external environment, i.e., swells substantially below a pH of about 6.0 and deswells at pH levels from about 7 to 14. However, additives and/or excipients may be added to either retard or enhance swelling or deswelling properties thereby controlling the swelling and/or deswelling behavior of the polymer blend internally. For example, by adding an acidic substance such as citric acid, tartaric acid, malic acid, maleic acid, etc., swelling may be prolonged or accelerated, even in some basic external environments. Conversely, by adding a basic substance such as sodium carbonate, magnesium hydroxide, disodium phosphate, etc., swelling may be retarded or deswelling may be accelerated, even in an acidic external environment.

To further illustrate the concept of internal control, if one wishes to override the time delay for stomach acids to enter a drug containing polymer blend and cause swelling, one might add citric acid into the blend causing the drug containing polymer blend to immediately become acidic as soon as water enters. Conversely, if one wanted to accelerate deswelling, a basic component may be added to the drug containing polymer blend.

Though it is contemplated that these polymer blends or hydrogels will be taken orally in a device or in tablet or capsule form, or, the use of these polymer blends or hydrogels is not limited to oral ingestion. These polymer blends or hydrogels may be used in a variety of other applications (i.e. rectally, vaginally, or implanted depending on the conditions to be treated). For example, tablets can be made for oral ingestion, suppositories can be made for insertion into the rectum or vagina or implantable capsules can be formed that are placed under the skin or in the peritoneal cavity. In each of these scenarios, the device would contain a hydrogel of the present invention. Further, though one preferred embodiment is to administer the combined drug and polymer blends in the dry state orally, allowing the acidic environment of the stomach to hydrate and swell the polymer blends to hydrogels and the alkaline environment of the intestines to deswell the hydrogel releasing drug, the polymer blends may also be hydrated prior to administration.

EXAMPLES

The examples that follow are representative of the various polymer blends made using the aforementioned procedures, but should not be considered as limitations of the present invention. Though specific degrees of deacetylation are shown in each example, deacetylated chitosan of other percentages may also be used. For example, though deacetylation as low as about 70% is shown, less than 70% deacetylation can also be used. For example, a homogenous acetylated chitosan at as low as 50% deacetylation is soluble at neutral pH and can be used within the context of the present invention.

Example 1

In all cases, 15 g of chitosan were dissolved per one liter of 1.0 M acetic acid solution, then the polyethylene glycol was added as needed to achieve the ratios illustrated in Table 1 and Table 2 below. Polyethylene glycol (Mw =2000, 18,500 or 4,000,000) and 85% deacetylated chitosan (Brookfield viscosity=440 cps, 535cps, or 810 cps) were each dissolved in 1.0 M aqueous acetic acid to form solutions that were then dried to form brittle solids. These solids were placed into acidified water (aqueous HCl having a pH of 2.0) and the swelling behavior characterized. The swollen samples were then transferred into alkaline water (Sorensens phosphate buffer having a pH of 7.4) where the deswelling behavior was characterized as a function of time. The following samples were characterized and the results were listed in Table 1 and Table 2 as follows:

TABLE 1

| Chitosan* (grams): PEG** (grams) | Swelling Performance |
| --- | --- |
| 20:1 | Marginally Acceptable (dissolves at pH 2 in 2 hours) |
| 10:1 | Acceptable (dissolves at pH 2 in approximately 4 hours) |
| 4:1 | Acceptable (does not dissolve after 24 hours at pH 2) |
| 2:1 | Acceptable (does not dissolve after 24 hours at pH 2) |
| 1:1 | Acceptable (does not dissolve after 24 hours at pH 2) |
| 1:2 | Acceptable (dissolves at pH 2 in approximately 6 hours) |
| 1:4 | Acceptable (dissolves at pH 2 in approximately 4 hours |

Solvent 1.0 M acetic acid in water
Chitosan*: deacetylation = 85%; Brookfield viscosity = 440 cps or 535 cps
PEG**: polyethylene glycol Mw = 2,000

TABLE 2

| Chitosan*:PEG** | PEG Mw | Chitosan cps | Swelling Performance |
| --- | --- | --- | --- |
| 4:1, 2:1, 1:1 | 2,000 | 440 | Acceptable |
| 4:1, 2:1, 1:1 | 2,000 | 535 | Acceptable |
| 4:1, 2:1, 1:1 | 2,000 | 810 | Acceptable |
| 4:1, 2:1, 1:1 | 18,500 | 440 | Acceptable |
| 4:1, 2:1, 1:1 | 18,500 | 535 | Acceptable |
| 4:1, 2:1, 1:1 | 4,000,000 | 440 | Acceptable |
| 4:1, 2:1, 1:1 | 4,000,000 | 535 | Acceptable |

Chitosan* = g of 85% deacetylated chitosan
PEG** = g of polyethylene glycol

All combinations marked "Acceptable" form a brittle solid in the dry state that swells rapidly (less than 2 hours) and extensively (25 to 50-fold) in acidified water (2.0 pH) without dissolving, and slowly deswells (80 to 90% in 6 to 12 hours) in alkaline water (pH 7.4) without dissolving. The rate of deswelling increases as the PEG (polyethylene glycol) content increases.

Example 2

Polyethylene glycol (Mw=2,000) and chitosan (85% deacetylated; Brookfield viscosity=535 cps) were dissolved in various aqueous acetic acid solutions (0.1 M, 0.2 M, 0.3 M, 0.5 M, 1.0 M, 2.0 M) to form polymer blend solutions that were then dried to form brittle solids. In all cases, 15 g of chitosan were dissolved per one liter of acetic acid solution, then 7.5 g polyethylene glycol were added. These solids were placed into acidified water (aqueous HCl having a pH of 2) for 2 hours and the swelling behavior characterized. The swollen samples were then transferred into alkaline water (pH=7.4) where the deswelling behavior was characterized as a function of time. The solids swelled in acidified water (pH=2) without dissolving when the concentration of acetic acid was increased above 0.5 M.

Example 3

Cellulose acetate (Mw=30,000) and chitosan (85% deacetylated; Brookfield viscosity=440 cps) were dissolved in 11 M acetic acid in water and then dried to form a brittle solid. The following ratios in grams of chitosan to grams of cellulose acetate have shown desired behavior: 1:1, 2:1 and 4:1. All combinations form a brittle solid in the dry state and swell rapidly (less than 2 hours) and extensively (5 to 30-fold) in acidified water (pH 2.0) without dissolving, and deswell (50 to 80%) slowly (6 to 12 hours) in alkaline water (pH 7.4) without dissolving. The rate of deswelling increases as the cellulose acetate content increases.

Example 4

Poloxamer (Mw=8,750; PEO:PPO=5g:1g) and chitosan (85% deacetylated; Brookfield viscosity=535 cps) were dissolved in 1 M acetic acid in water and then dried to form a brittle solid. The chitosan to poloxamer weight ratio of 2:1 has shown the desired swelling/deswelling behavior. This combination forms a brittle solid in the dry state and swells rapidly (less than 2 hours) and extensively (40 to 45-fold) in acidified water (pH 2.0) without dissolving, and deswells (80 to 90%) slowly (6 to 12 hours) in alkaline water (pH 7.4) without dissolving.

Example 5

Dextran (Mw=10,000) and chitosan (85% deacetylated; Brookfield viscosity=535 cps) were dissolved in 1 M acetic acid and then dried to form a brittle solid. The chitosan to dextran weight ratio of 2:1 has shown the desired swelling/deswelling behavior. The combination formed a brittle solid in the dry state that swelled rapidly (less than 6 hours) and extensively (50 to 55-fold) in acidified water (pH 2.0) without dissolving, and deswelled (50 to 60%) slowly (13 hours) in alkaline water (pH 7.4) without dissolving.

Example 6

Polyvinylpyrrolidone (Mw=360,000) and chitosan (85% deacetylated; Brookfield viscosity=535 cps) were dissolved in 1 M aqueous acetic acid and then dried to form a brittle solid. The chitosan:PVP (polyvinylpyrrolidone) weight ratio of 2:1 has shown the desired swelling/deswelling behavior. This combination formed a brittle solid in the dry state that swelled rapidly (less than 3 hours) and extensively (110 to 115-fold) in acidified water (pH 2.0) without dissolving, and deswelled (80 to 90%) slowly (9 to 12 hours) in alkaline water (pH 7.4) without dissolving. Exposure of this combination to pH 2.0 for more than 4 hours resulted in substantial dissolution.

Example 7

Polyvinyl alcohol (Mw=78,000) and chitosan (85% deacetylated; Brookfield viscosity=535 cps) were dissolved in 1 M aqueous acetic acid and then dried to form a brittle solid. The chitosan:PVA (polyvinyl alcohol) weight ratio of 2:1 has shown the desired swelling/deswelling behavior. This combination formed a brittle solid in the dry state that swelled rapidly (less than 0.4 hours) and extensively (25 to 40-fold) in acidified water (pH 2.0) without dissolving, and deswelled (10 to 20%) slowly (2 hours) in alkaline water (pH 7.4) without dissolving.

Example 8

About 15 grams of 76% deacetylated chitosan having a Brookfield viscosity of 1693 was dissolved in one liter of a 1.0 M aqueous acetic acid solution. Next, about 7.5 grams of polyethylene glycol (Mw=3350) were added to form a polymer blend solution. The solution was dried to form a brittle solid.

The brittle solid was placed in an acidified aqueous media (simulated gastric fluid, pH=1.2) for 2 hours and the swelling behavior was characterized. After two hours of contact between the brittle solid and the acidified aqueous media hydrogel that had swollen to about 70 times the size of the brittle solid was observed. The swollen sample was then transferred into an alkaline aqueous media (simulated intestinal fluid, pH=7.4) where the deswelling from hour 3 to hour 24 was characterized. The deswelling was quantified in Table 3 below where the swelling ratio was compared to the original size of the brittle solid prior to swelling in the acidified aqueous media, i.e., swelling ratio=weight of hydrated film/weight of dry film.

TABLE 3

| TIME (hr) | SWELLING RATIO |
|---|---|
| 3 | 50 |
| 4 | 41 |
| 5 | 36 |
| 6 | 33 |
| 7 | 32 |
| 8 | 31 |
| 12 | 25 |

TABLE 3-continued

| TIME (hr) | SWELLING RATIO |
|---|---|
| 16 | 21 |
| 20 | 20 |
| 24 | 18 |

Thus, the brittle solid formed a hydrogel and swelled quickly in the acidic aqueous media without dissolving and deswelled slowly over time when placed in the basic aqueous media.

Example 9

About 15 grams of 71% deacetylated chitosan having a Brookfield viscosity of 2173 was dissolved in one liter of a 1.0 M aqueous acetic acid solution. Next, about 7.5 grams of polyethyene glycol=3350) were added to form a polymer blend solution was dried to form a brittle solid.

The brittle dolis was placed in an acidified aqueous media (simulated gastric fluid, pH=1.2) for 2 hours and the swelling behavior was characterized. At two hours, the hydrogel formed from the brittle solid had swollen to about 62 times its original size. The swollen sample was then transferred into an alkaline aqueous media (simulated intestinal fluid, pH=7.4) where the deswelling from hour 3 to hour 24 was characterized. The deswelling was quantified in Table 4 below where the swelling ratio was calculated as a comparison to the original brittle solid size prior to swelling in the acidified aqueous media, i.e., swelling ratio=weight of hydrated film/weight of dry film.

TABLE 4

| TIME (hr) | SWELLING RATIO |
|---|---|
| 3 | 57 |
| 4 | 53 |
| 5 | 49 |
| 6 | 45 |
| 7 | 42 |
| 8 | 39 |
| 12 | 31 |
| 16 | 27 |
| 20 | 25 |
| 24 | 23 |

Thus, the brittle solid formed a hydrogel that swelled quickly in the acidic aqueous media without dissolving and deswelled slowly over time when placed in the basic aqueous media.

Example 10

About 15 grams of 74% deacetylated chitosan having a Brookfield viscosity of 2390 was dissolved in one liter of a 1.0 M aqueous acetic acid solution. Next, about 7.5 grams of polyethylene glycol (Mw=3350) were added to form a polymer blend solution. The solution was dried to form a brittle solid.

The brittle solid was placed in an acidified aqueous media (simulated gastric fluid, pH=1.2) for 2 hours and the swelling behavior was characterized. After two hours of contact between the brittle solid and the acidified aqueous media, the hydrogel had swollen to about 57 times the size of the brittle solid was observed. The swollen sample was then transferred into an alkaline aqueous media (simulated intestinal fluid, pH=7.4) where the deswelling from hour 3 to hour 24 was characterized. The deswelling was characterized in Table 5 below where the swelling ratio is compared to the original brittle solid size prior to swelling in the acidified aqueous media, i.e., swelling ratio=weight of hydrated film/weight of dry film.

TABLE 5

| TIME (hr) | SWELLING RATIO |
|---|---|
| 3 | 52 |
| 4 | 47 |
| 5 | 44 |
| 6 | 42 |
| 7 | 40 |
| 8 | 39 |
| 12 | 33 |
| 16 | 28 |
| 20 | 26 |
| 24 | 23 |

Thus, the brittle solid formed a hydrogel and swelled quickly in the acidic aqueous media without dissolving and a deswelled slowly over time when placed in the basic aqueous media.

Example 11

About 15 grams of 72% deacetylated chitosan having a Brookfield viscosity of 3460 was dissolved in one liter of a 1.0 M aqueous acetic acid solution. Next, about 7.5 grams of polyethylene glycol (Mw=3350) were added to form a polymer blend solution. The solution was dried to form a brittle solid.

The brittle solid was placed in an acidified aqueous media (simulated gastric fluid, pH=1.2) for 2 hours and the swelling behavior was characterized. At two hours, the hydrogel formed from the brittle solid had swollen to about 55 times its original size. The swollen sample was then transferred into an alkaline aqueous media (simulated intestinal fluid, pH=7.4) where the deswelling from hour 3 to hour 24 was characterized. The deswelling was characterized in Table 6 below where the swelling ratio was compared to the original brittle solid size prior to swelling in the acidified aqueous media, i.e., swelling ratio =weight of hydrated film/weight of dry film.

TABLE 6

| TIME (hr) | SWELLING RATIO |
|---|---|
| 3 | 52 |
| 4 | 47 |
| 5 | 44 |
| 6 | 42 |
| 7 | 41 |
| 8 | 39 |
| 12 | 33 |
| 16 | 30 |
| 20 | 28 |
| 24 | 26 |

Thus, the brittle solid formed a hydrogel and swelled quickly in the acidic aqueous media without dissolving and deswelled slowly over time when placed in the basic aqueous media.

Example 12

Various drugs have been mixed with the polymer blends of the I0 present invention by first, dissolving or suspending the drug in the acidic solution of chitosan and a second polymer selected from the group consisting of polyether glycols (e.g., polyethylene glycols), cellulose esters (e.g., cellulose acetate), poloxamers, polysaccharides (e.g., dextran and guar), polyvinylpyrrolidones, polyvinyl alcohols, and mixtures or copolymers thereof. These mixtures were then dried to form brittle solids that were ground or milled into a powder or particulate form for easy incorporation into tablet shaped dosage forms.

As the drug laden polymer blend was hydrated and swelled in response to an acidic environment, the diffusional distance increased and the escape of the drug from the hydrogel was slowed. As the hydrogel deswelled in response to a more neutral to basic environment, the drug was released convectively.

A simple variant of this method is to preswell drug-free, dry hydrogel particles in an acidic aqueous solution of the drug. The drug will equilibrate into the swollen hydrogel matrix. The swollen hydrogel is then isolated and dried resulting in a drug-laden hydrogel powder. As a preferred embodiment, the powder may then be orally ingested where the acidic environment of the stomach causes the drug/polymer blend powders to form a drug laden hydrogel.

Example 13

Various drugs have been mixed with the polymer blends of the present invention. This was normally done by first, forming a polymer blend comprised of chitosan and a second polymer selected from the group consisting of polyether glycols (e.g., polyethylene glycols), cellulose esters (e.g., cellulose acetate), poloxamers, polysaccharides (e.g., dextran and guar), polyvinylpyrrolidones, polyvinyl alcohols, and mixtures or copolymers thereof. The polymer blend was then pulverized to form a powder or particulate material. To this dried powder or particulate polymer blend, a drug powder was admixed forming a homogenous mixture of dry hydrogel particles and dry drug particles. This mixture is easily incorporated into tablet shaped dosage forms.

As the dry polymer blend/drug particles hydrated and swelled in response to an acidic environment, the diffusional resistance for drug transport increased and the escape of the drug from the tablet was slow due to the swollen hydrogel. As the hydrogel deswelled in response to more neutral to basic environments, including environments that fall into the basic range (i.e. >pH 7), the drug released more rapidly as the diffusional resistance was reduced. Compositions that demonstrate this behavior are listed in Table 7 as follows:

TABLE 7

| Drug (mgs) (Buspirone·HCl) | Hydrogel (mgs) (chitosan*:PEG at 2 g:1 g) | Excipient (mgs) (sorbitol; q.s. 150 mg total tablet** weight) |
|---|---|---|
| 10 | 1.5 | 148.5 |
| 10 | 3 | 147.0 |
| 10 | 4.5 | 145.5 |
| 10 | 7.5 | 142.5 |

*chitosan = 85% deacetylation; Brookfield viscosity = 535 cps
**tablets coated with porous coating; drug release was slower as the hydrogel content increased, indicating the hydrogel was rate controlling.

Table 7 shows that the hydrogels of the present invention are capable of controlling the release of bioactive agents or drugs into a physiological environment, particularly into the gastrointestinal tract.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A polymer blend drug composition that, when exposed to aqueous conditions, swells in an acidic environment and deswells in a more neutral or basic environment comprising a therapeutically effective amount of a drug combined with a polymer blend, said polymer blend comprising chitosan and a second polymer, wherein said chitosan and said second polymer are not covalently or ionically crosslinked, and wherein said second polymer is a polyethylene glycol having a weight average molecular weight (Mw) from 1,000 to 4,000,000.

2. A polymer blend drug composition as in claim 1 wherein said polyethylene glycol has a weight average molecular weight (Mw) from about 1,000 to 6,000.

3. A polymer blend drug composition that, when exposed to aqueous conditions, swells in an acidic environment and deswells in a more neutral or basic environment comprising a therapeutically effective amount of a drug combined with a polymer blend, said polymer blend comprising chitosan and a second polymer, wherein said chitosan and said second polymer are not covalently or ionically crosslinked, and wherein said second polymer is a cellulose acetate having a weight average molecular weight (Mw) from about 10,000 to 50,000.

4. A polymer blend drug composition that, when exposed to aqueous conditions, swells in an acidic environment and deswells in a more neutral or basic environment comprising a therapeutically effective amount of a drug combined with a polymer blend, said polymer blend comprising chitosan and a second polymer, wherein said chitosan and said second polymer are not covalently or ionically crosslinked, and wherein said second polymer is a poloxamer having a weight average molecular weight (Mw) from about 1,000 to 12,000.

5. A polymer blend drug composition that, when exposed to aqueous conditions, swells in an acidic environment and deswells in a more neutral or basic environment comprising a therapeutically effective amount of a drug combined with a polymer blend, said polymer blend comprising chitosan and a second polymer, wherein said chitosan and said second polymer are not covalently or ionically crosslinked, and wherein said second polymer is a dextran having a weight average molecular weight (Mw) from about 10,000 to 4,000,000.

6. A polymer blend drug composition that, when exposed to aqueous conditions, swells in an acidic environment and deswells in a more neutral or basic environment comprising a therapeutically effective amount of a drug combined with a polymer blend, said polymer blend comprising chitosan and a second polymer, wherein said chitosan and said second polymer are not covalently or ionically crosslinked, and wherein said second polymer is a polyvinyl alcohol having a weight average molecular weight (Mw) from about 5,000 to 200,000.

7. A polymer blend drug composition as in claim 1 wherein said polymer blend is prepared by dissolving said chitosan and said second polymer in an acidic aqueous solution to form an aqueous polymer blend, dehydrating said aqueous polymer blend, and recovering said polymer blend.

8. A polymer blend drug composition as in claim 7 wherein said acidic aqueous solution comprises water and an acidifying agent selected from the group consisting of acetic acid, citric acid, hydrochloric acid, and combinations thereof, and wherein said acidic aqueous solution has a concentration from about 0.5 M to 11 M.

9. A polymer blend drug composition as in claim 1 wherein said chitosan to said second polymer weight ratio is from about 1:4 to 10:1.

10. A polymer blend drug composition as in claim 1 wherein said chitosan has a Brookfield viscosity from about 100 cps to 10,000 cps.

11. A polymer blend drug composition as in claim 10 wherein said chitosan has a Brookfield viscosity from about 440 cps to 3460 cps.

12. A polymer blend drug composition as in claim 1 wherein said chitosan is from 50% to 95% deacetylated.

13. A polymer blend drug composition as in claim 1 wherein said drug is combined with said chitosan and said second polymer by dissolving said drug, said chitosan, and said second polymer in the acidic aqueous solution to form a drug containing aqueous polymer blend, and dehydrating and grinding said drug containing aqueous polymer blend to form a particulate drug containing polymer blend.

14. A polymer blend drug composition as in claim 1 wherein said drug is combined with said chitosan and said second polymer by swelling said polymer blend in an acidic solution containing said drug, equilibrating said swollen polymer blend and said drug, and dehydrating said swollen polymer blend containing said drug.

15. A polymer blend drug composition as in claim 1 wherein said drug is combined with said chitosan and said second polymer by admixing said drug in a particulate form with said polymer blend in a particulate form.

16. A polymer blend drug composition as in claim 1 wherein pH controlling additives or excipients are admixed with said polymer blend to alter the swelling and deswelling properties of said polymer blend.

17. A polymer blend drug composition as in claim 16 wherein said additive is an acidic particulate selected from the group consisting of citric acid, tartaric acid, malic acid, maleic acid, and combinations thereof, and wherein said additive prolongs or accelerates the swelling of said drug containing polymer blend.

18. A polymer blend drug composition as in claim 16 wherein said additive is a basic particulate selected from the group consisting of sodium carbonate, magnesium hydroxide, disodium phosphate, and combinations thereof, and wherein said additive retards the swelling or accelerates the deswelling of said drug containing polymer blend.

19. A polymer blend drug composition as in claim 3 wherein said polymer blend is prepared by dissolving said chitosan and said second polymer in an acidic aqueous solution to form an aqueous polymer blend, dehydrating said aqueous polymer blend, and recovering said polymer blend.

20. A polymer blend drug composition as in claim 19 wherein said acidic aqueous solution comprises water and an acidifying agent selected from the group consisting of acetic acid, citric acid, hydrochloric acid, and combinations thereof, and wherein said acidic aqueous solution has a concentration from about 0.5 M to 11 M.

21. A polymer blend drug composition as in claim 3 wherein said chitosan to said second polymer weight ratio is from about 1:4 to 10:1.

22. A polymer blend drug composition as in claim 3 wherein said chitosan has a Brookfield viscosity from about 100 cps to 10,000 cps.

23. A polymer blend drug composition as in claim 22 wherein said chitosan has a Brookfield viscosity from about 440 cps to 3460 cps.

24. A polymer blend drug composition as in claim 3 wherein said chitosan is from 50% to 95% deacetylated.

25. A polymer blend drug composition as in claim 3 wherein said drug is combined with said chitosan and said second polymer by dissolving said drug, said chitosan, and said second polymer in the acidic aqueous solution to form a drug containing aqueous polymer blend, and dehydrating and grinding said drug containing aqueous polymer blend to form a particulate drug containing polymer blend.

26. A polymer blend drug composition as in claim 3 wherein said drug is combined with said chitosan and said second polymer by swelling said polymer blend in an acidic solution containing said drug, equilibrating said swollen polymer blend and said drug, and dehydrating said swollen polymer blend containing said drug.

27. A polymer blend drug composition as in claim 3 herein said drug is combined with said chitosan and said second polymer by admixing said drug in a particulate form with said polymer blend in a particulate form.

28. A polymer blend drug composition as in claim 3 wherein pH controlling additives or excipients are admixed with said polymer blend to alter the swelling and deswelling properties of said polymer blend.

29. A polymer blend drug composition as in claim 28 wherein said additive is an acidic particulate selected from the group consisting of citric acid, tartaric acid, malic acid, maleic acid, and combinations thereof, and wherein said additive prolongs or accelerates the swelling of said drug containing polymer blend.

30. A polymer blend drug composition as in claim 28 wherein said additive is a basic particulate selected from the group consisting of sodium carbonate, magnesium hydroxide, disodium phosphate, and combinations thereof, and wherein said additive retards the swelling or accelerates the deswelling of said drug containing polymer blend.

31. A polymer blend drug composition as in claim 4 wherein said polymer blend is prepared by dissolving said chitosan and said second polymer in an acidic aqueous solution to form an aqueous polymer blend, dehydrating said aqueous polymer blend, and recovering said polymer blend.

32. A polymer blend drug composition as in claim 31 wherein said acidic aqueous solution comprises water and an acidifying agent selected from the group consisting of acetic acid, citric acid, hydrochloric acid, and combinations thereof, and wherein said acidic aqueous solution has a concentration from about 0.5 M to 11 M.

33. A polymer blend drug composition as in claim 4 wherein said chitosan to said second polymer weight ratio is from about 1:4 to 10:1.

34. A polymer blend drug composition as in claim 4 wherein said chitosan has a Brookfield viscosity from about 100 cps to 10,000 cps.

35. A polymer blend drug composition as in claim 34 wherein said chitosan has a Brookfield viscosity from about 440 cps to 3460 cps.

36. A polymer blend drug composition as in claim 4 wherein said chitosan is from 50% to 95% deacetylated.

37. A polymer blend drug composition as in claim 4 wherein said drug is combined with said chitosan and said second polymer by dissolving said drug, said chitosan, and said second polymer in the acidic aqueous solution to form a drug containing aqueous polymer blend, and dehydrating and grinding said drug containing aqueous polymer blend to form a particulate drug containing polymer blend.

38. A polymer blend drug composition as in claim 4 wherein said drug is combined with said chitosan and said second polymer by swelling said polymer blend in an acidic solution containing said drug, equilibrating said swollen polymer blend and said drug, and dehydrating said swollen polymer blend containing said drug.

39. A polymer blend drug composition as in claim 4 wherein said drug is combined with said chitosan and said second polymer by admixing said drug in a particulate form with said polymer blend in a particulate form.

40. A polymer blend drug composition as in claim 4 wherein pH controlling additives or excipients are admixed with said polymer blend to alter the swelling and deswelling properties of said polymer blend.

41. A polymer blend drug composition as in claim 40 wherein said additive is an acidic particulate selected from the group consisting of citric acid, tartaric acid, malic acid, maleic acid, and combinations thereof, and wherein said additive prolongs or accelerates the swelling of said drug containing polymer blend.

42. A polymer blend drug composition as in claim 40 wherein said additive is a basic particulate selected from the group consisting of sodium carbonate, magnesium hydroxide, disodium phosphate, and combinations thereof, and wherein said additive retards the swelling or accelerates the deswelling of said drug containing polymer blend.

43. A polymer blend drug composition as in claim 5 wherein said polymer blend is prepared by dissolving said chitosan and said second polymer in an acidic aqueous solution to form an aqueous polymer blend, dehydrating said aqueous polymer blend, and recovering said polymer blend.

44. A polymer blend drug composition as in claim 43 wherein said acidic aqueous solution comprises water and an acidifying agent selected from the group consisting of acetic acid, citric acid, hydrochloric acid, and combinations thereof, and wherein said acidic aqueous solution has a concentration from about 0.5 M to 11 M.

45. A polymer blend drug composition as in claim 5 wherein said chitosan to said second polymer weight ratio is from about 1:4 to 10:1.

46. A polymer blend drug composition as in claim 5 wherein said chitosan has a Brookfield viscosity from about 100 cps to 10,000 cps.

47. A polymer blend drug composition as in claim 46 wherein said chitosan has a Brookfield viscosity from about 440 cps to 3460 cps.

48. A polymer blend drug composition as in claim 5 wherein said chitosan is from 50% to 95% deacetylated.

49. A polymer blend drug composition as in claim 5 wherein said drug is combined with said chitosan and said second polymer by dissolving said drug, said chitosan, and said second polymer in the acidic aqueous solution to form a drug containing aqueous polymer blend, and dehydrating and grinding said drug containing aqueous polymer blend to form a particulate drug containing polymer blend.

50. A polymer blend drug composition as in claim 5 wherein said drug is combined with said chitosan and said second polymer by swelling said polymer blend in an acidic solution containing said drug, equilibrating said swollen polymer blend and said drug, and dehydrating said swollen polymer blend containing said drug.

51. A polymer blend drug composition as in claim 5 wherein said drug is combined with said chitosan and said second polymer by admixing said drug in a particulate form with said polymer blend in a particulate form.

52. A polymer blend drug composition as in claim 5 wherein pH controlling additives or excipients are admixed with said polymer blend to alter the swelling and deswelling properties of said polymer blend.

53. A polymer blend drug composition as in claim 52 wherein said additive is an acidic particulate selected from the group consisting of citric acid, tartaric acid, malic acid, maleic acid, and combinations thereof, and wherein said additive prolongs or accelerates the swelling of said drug containing polymer blend.

54. A polymer blend drug composition as in claim 52 wherein said additive is a basic particulate selected from the group consisting of sodium carbonate, magnesium hydroxide, disodium phosphate, and combinations thereof, and wherein said additive retards the swelling or accelerates the deswelling of said drug containing polymer blend.

55. A polymer blend drug composition as in claim 6 wherein said polymer blend is prepared by dissolving said chitosan and said second polymer in an acidic aqueous solution to form an aqueous polymer blend, dehydrating said aqueous polymer blend, and recovering said polymer blend.

56. A polymer blend drug composition as in claim 55 wherein said acidic aqueous solution comprises water and an acidifying agent selected from the group consisting of acetic acid, citric acid, hydrochloric acid, and combinations thereof, and wherein said acidic aqueous solution has a concentration from about 0.5 M to 11 M.

57. A polymer blend drug composition as in claim 6 wherein said chitosan to said second polymer weight ratio is from about 1:4 to 10:1.

58. A polymer blend drug composition as in claim 6 wherein said chitosan has a Brookfield viscosity from about 100 cps to 10,000 cps.

59. A polymer blend drug composition as in claim 58 wherein said chitosan has a Brookfield viscosity from about 440 cps to 3460 cps.

60. A polymer blend drug composition as in claim 6 wherein said chitosan is from 50% to 95% deacetylated.

61. A polymer blend drug composition as in claim 6 wherein said drug is combined with said chitosan and said second polymer by dissolving said drug, said chitosan, and said second polymer in the acidic aqueous solution to form a drug containing aqueous polymer blend, and dehydrating and grinding said drug containing aqueous polymer blend to form a particulate drug containing polymer blend.

62. A polymer blend drug composition as in claim 6 wherein said drug is combined with said chitosan and said second polymer by swelling said polymer blend in an acidic solution containing said drug, equilibrating said swollen polymer blend and said drug, and dehydrating said swollen polymer blend containing said drug.

63. A polymer blend drug composition as in claim 6 wherein said drug is combined with said chitosan and said second polymer by admixing said drug in a particulate form with said polymer blend in a particulate form.

64. A polymer blend drug composition as in claim 6 wherein pH controlling additives or excipients are admixed with said polymer blend to alter the swelling and deswelling properties of said polymer blend.

65. A polymer blend drug composition as in claim 64 wherein said additive is an acidic particulate selected from the group consisting of citric acid, tartaric acid, malic acid, maleic acid, and combinations thereof, and wherein said additive prolongs or accelerates the swelling of said drug containing polymer blend.

66. A polymer blend drug composition as in claim 64 wherein said additive is a basic particulate selected from the group consisting of sodium carbonate, magnesium hydroxide, disodium phosphate, and combinations thereof, and wherein said additive retards the swelling or accelerates the deswelling of said drug containing polymer blend.

* * * * *